United States Patent
Akagawa (10) Patent No.: US 12,070,329 B2
(45) Date of Patent: Aug. 27, 2024

(54) OPTICAL MEASUREMENT METHOD, OPTICAL MEASUREMENT APPARATUS, AND NON-TRANSITORY COMPUTER READABLE MEDIUM

(71) Applicant: NEC Corporation, Tokyo (JP)

(72) Inventor: Takeshi Akagawa, Tokyo (JP)

(73) Assignee: NEC CORPORATION, Tokyo (JP)

( * ) Notice: Subject to any disclaimer, the term of this patent is extended or adjusted under 35 U.S.C. 154(b) by 191 days.

(21) Appl. No.: 17/801,852

(22) PCT Filed: Mar. 19, 2020

(86) PCT No.: PCT/JP2020/012428
§ 371 (c)(1),
(2) Date: Aug. 24, 2022

(87) PCT Pub. No.: WO2021/186703
PCT Pub. Date: Sep. 23, 2021

(65) Prior Publication Data
US 2023/0080382 A1    Mar. 16, 2023

(51) Int. Cl.
*A61B 5/00* (2006.01)
*G01B 9/02091* (2022.01)
*G06T 11/60* (2006.01)

(52) U.S. Cl.
CPC .......... *A61B 5/4887* (2013.01); *A61B 5/0066* (2013.01); *A61B 5/441* (2013.01); *G01B 9/02091* (2013.01); *G06T 11/60* (2013.01); *A61B 5/742* (2013.01)

(58) Field of Classification Search
CPC ..... A61B 5/4887; A61B 5/0066; A61B 5/441; A61B 5/742; G01B 9/02091; G06T 11/60
See application file for complete search history.

(56) References Cited

U.S. PATENT DOCUMENTS

2016/0225141 A1  8/2016  Hattersley et al.
2016/0262624 A1  9/2016  Nakajima et al.

FOREIGN PATENT DOCUMENTS

| JP | 2006-000385 A | 1/2006 |
| JP | 2016-054986 A | 4/2016 |
| JP | 2016-526978 A | 9/2016 |
| JP | 2017-023474 A | 2/2017 |
| WO | 2015/060376 A1 | 4/2015 |

OTHER PUBLICATIONS

International Search Report for PCT Application No. PCT/JP2020/012428, mailed on Jun. 16, 2020.

*Primary Examiner* — Chao Sheng
(74) *Attorney, Agent, or Firm* — Sughrue Mion, PLLC (57) ABSTRACT

An object of the present disclosure is to provide an optical measurement method, an optical measurement apparatus, and a non-transitory computer readable medium capable of specifying the position of a pore. The optical measurement method includes first, second, and third steps. In the first step (ST11), first 3D tomographic image data is acquired from a skin by using optical coherence tomography. In the second step (ST12), a line shown in a second planar image (B2) at a second depth is removed from a first planar image (B1) at a first depth, the second depth being deeper than the first depth. In the third step (ST13), a position of a pore is specified from the first planar image (B1) from which the line has been removed.

12 Claims, 10 Drawing Sheets

OPTICAL MEASUREMENT METHOD, OPTICAL MEASUREMENT APPARATUS, AND NON-TRANSITORY COMPUTER READABLE MEDIUM

This application is a National Stage Entry of PCT/JP2020/012428 filed on Mar. 19, 2020, the contents of all of which are incorporated herein by reference, in their entirety.

TECHNICAL FIELD

The present invention relates to an optical measurement method, an optical measurement apparatus, and a non-transitory computer readable medium.

BACKGROUND ART

For performing optical measurement, there are a wide variety of technologies including, for example, optical ultrasound technologies, technologies using confocal microscopes, optical coherence tomography, and the like. As an example of these technologies, Patent Literature 1 discloses a method for processing optical coherence tomography (OCT) scanning images of a skin of a subject having a surface. This method includes a step for acquiring a plurality of scanning images under (or inside) the skin of the subject. The plurality of scanning images are images showing OCT signals in a plurality of layers on parallel planes under the user's skin. The plurality of scanning images are shifted from each other in a direction perpendicular to the parallel planes. This method includes a step for determining a position on the surface of the skin in each of the scanning images.

CITATION LIST

Patent Literature

Patent Literature 1: Published Japanese Translation of PCT International Publication for Patent Application, No. 2016-526978

SUMMARY OF INVENTION

Technical Problem

However, in the above-described method, in some cases, it is impossible to specify the position of a pore on the surface of the skin because a hair is confused with an object, such as a foreign object, other than the hair.

In view of the above-described problem, an object of the present disclosure is to provide an optical measurement method, an optical measurement apparatus, and a non-transitory computer readable medium capable of specifying the position of a pore.

Solution to Problem

An optical measurement method according to an example embodiment of the present disclosure includes:
  a step of removing, from a first planar image at a first depth in a first three-dimensional tomographic image data acquired from a skin by using optical coherence tomography, a line shown in a second planar image at a second depth deeper than the first depth; and
  a step of specifying a position of a pore from the first planar image from which the line has been removed.

An optical measurement apparatus according to an example embodiment of the present disclosure includes:
  an image processing unit configured to remove, from a first planar image at a first depth in a first three-dimensional tomographic image data acquired from a skin by using optical coherence tomography, a line shown in a second planar image at a second depth deeper than the first depth; and
  a measurement processing unit configured to specify a position of a pore from the first planar image from which the line has been removed.

According to an example embodiment of the present disclosure, a non-transitory computer readable medium stores a program for causing a computer to perform:
  a step of removing, from a first planar image at a first depth in a first three-dimensional tomographic image data acquired from a skin by using optical coherence tomography, a line shown in a second planar image at a second depth deeper than the first depth; and
  a step of specifying a position of a pore from the first planar image from which the line has been removed.

Advantageous Effects of Invention

According to the present disclosure, it is possible to provide an optical measurement method, an optical measurement apparatus, and a non-transitory computer readable medium capable of specifying the position of a pore.

EXAMPLE EMBODIMENT

A specific example embodiment to which the present invention is applied will be described hereinafter in detail with reference to the drawings. However, the present invention is not limited to the below-shown example embodiment. Further, the following description and drawings are simplified as appropriate for clarifying the explanation.

Example Embodiment

Figure 1:
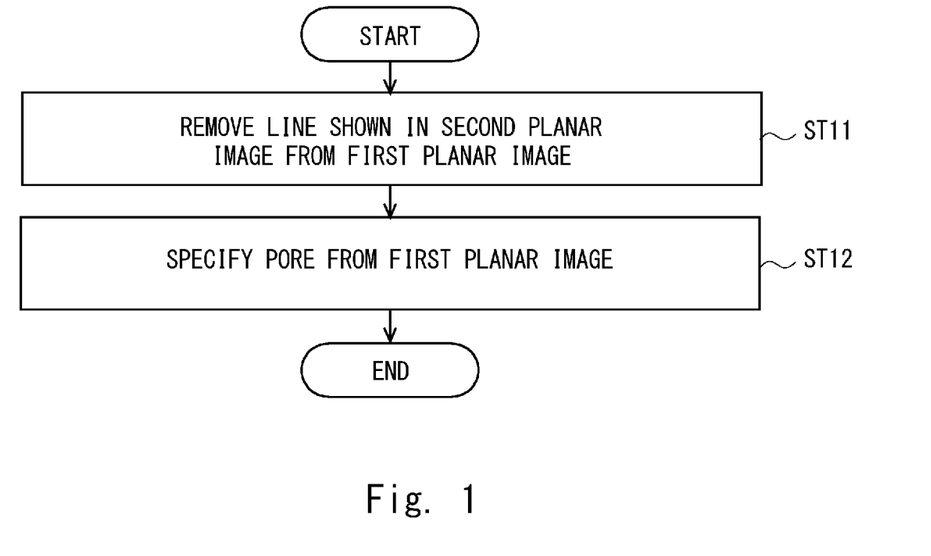
FIG. 1 is a flowchart showing an optical measurement method according to an example embodiment.

An optical measurement method according to an example embodiment will be described with reference to FIG. 1. FIG. 1 is a flowchart showing an optical measurement method according to an example embodiment.

In first 3D (three-dimensional) tomographic image data, from a first planar image at a first depth, lines shown in a second planar image at a second depth are removed (Step ST11).

The first 3D tomographic image data is acquired from a skin by using optical coherence tomography (OCT: Optical Coherence Tomography). This acquired first 3D tomographic image data includes a plurality of planar images including a planar image in the outermost surface of the skin and those inside the skin. The plurality of planar images include the first planar image at the first depth and the second planar image at the second depth. These planar images show planes substantially parallel to the outermost surface of the skin, located in a range from the outermost surface of the skin to a predetermined depth inside the skin.

The second depth is deeper than the first depth. The first depth is preferably one at which, in the plane shown by the first planar image, hairs extend (e.g., lie) on the plane. For example, the first depth preferably corresponds to the outermost surface of the skin. In many cases, lines shown in the first planar image indicate hairs, wrinkles, or foreign objects. The foreign objects are substances other than the skin, such as dirt, dust, and motes. The second depth is preferably a depth at which, in the plane shown by the second planar image, no hair extends (e.g., lies), and at which there may be wrinkles. In many cases, lines shown in the second planar image indicate wrinkles.

Lastly, the position(s) of a pore(s) is specified from the first planar image from which the above-described lines have been removed (Step ST12).

Thorough the above-described processes, it is possible to acquire the first planar image from which the lines indicating wrinkles have been removed. Therefore, it is possible to reduce the possibility that a winkle is mistakenly determined to be a hair, and thereby to reliably specify the position of a pore. Further, fine hairs or the like are less likely to be correctly specified as hairs compared to thick hairs. Such thick hairs are easily observed by the naked eye. Such fine hairs are not easily observed by the naked eye, and are, for example, downy hairs. Therefore, the above-described optical measurement method according to the first example embodiment is particularly preferred for uses in which the positions of such fine hairs need to be specified.

First Example Embodiment

Figure 2:
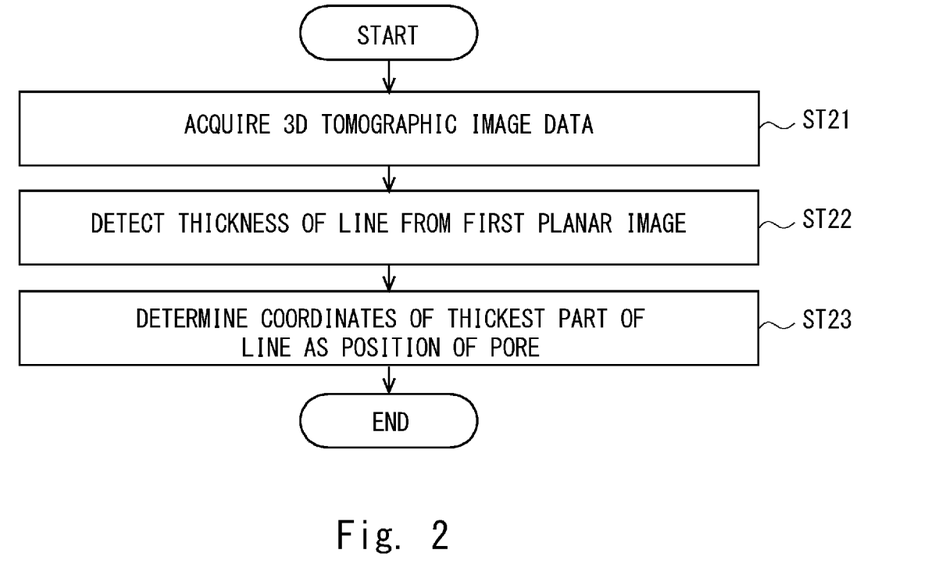
FIG. 2 is a flowchart showing an optical measurement method according to a first example embodiment.

An optical measurement method according to a first example embodiment will be described with reference to FIG. 2. FIG. 2 is a flowchart showing the optical measurement method according to the first example embodiment.

First 3D (three-dimensional) tomographic image data is acquired from a skin by using optical coherence tomography (Step ST21).

Next, the thickness of a line shown in the first planar image is detected (Step ST22). For example, the thicknesses of a plurality of parts of the line may be detected. Further, the widths at one end and the other end of the line shown in the first planar image may be measured, and the widths at the one end and the other end may be defined as the thicknesses of the one end and the other end of the line.

Lastly, the coordinates of the thickest part of the line, of which the thicknesses have been detected as described above, are determined as the position of the pore (Step ST23). In most cases, the root of a hair is thicker than the tip of the hair. One of the one end and the other end that is thicker than the other is determined as the root of the hair. For example, when one end is thicker than the other end, the one end is determined as the root of the hair.

Thorough the above-described processes, it is possible to specify the position of a pore from the first planar image in a mechanical manner.

Modified Example

Figure 3:
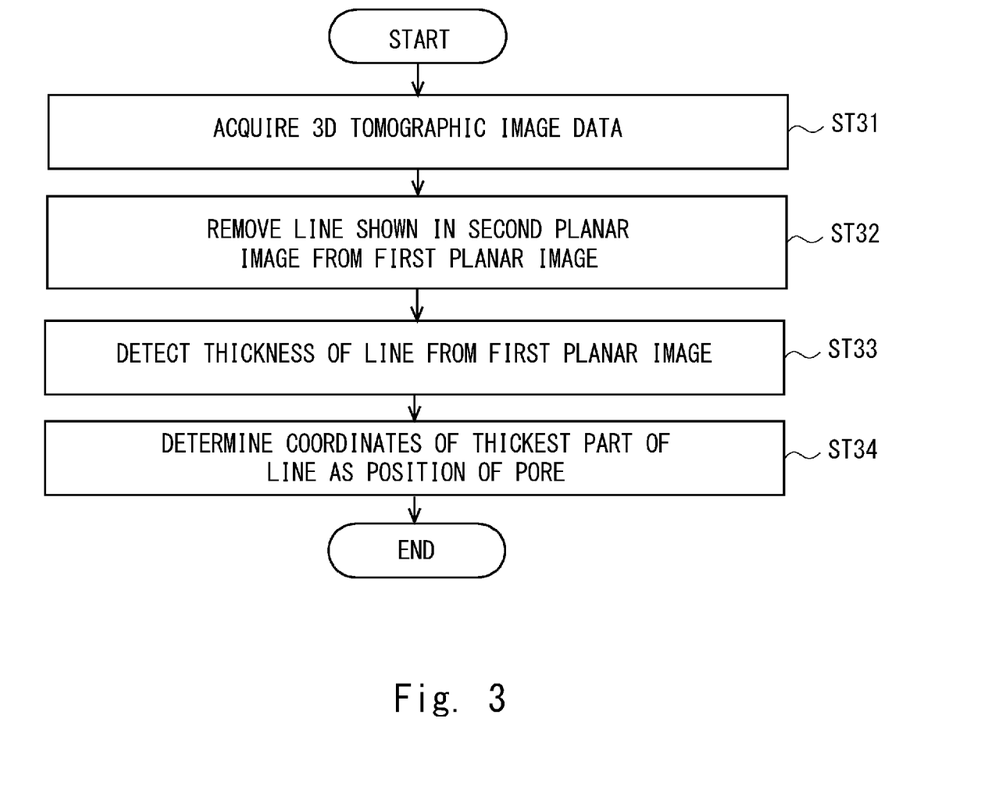
FIG. 3 is a flowchart showing a modified example of the optical measurement method according to the first example embodiment.

Note that, as a modified example of the optical measurement method according to the first example embodiment, there is an optical measurement method shown in a flow-chart shown in FIG. 3. This optical measurement method is a combination of a part of the optical measurement method according to the above-described example embodiment and a part of the optical measurement method according to the above-described first example embodiment.

Specifically, similarly to the step ST21, first 3D tomographic image data is acquired from a skin by using optical coherence tomography (Step ST31). Next, similarly to the step ST11, lines shown in the second planar image at the second depth are removed from the first planar image at the first depth (Step ST32). Next, similarly to the step ST22, the thickness of a line shown in the first planar image is detected (Step ST33). Lastly, similarly to the step ST23, the coordinates of the thickest part of the line, of which the thicknesses have been detected as described above, are determined as the position of the pore (Step ST34).

Thorough the above-described processes, it is possible to reduce the possibility that a winkle is mistakenly determined as a hair, and thereby to specify the position of a pore in a mechanical manner.

Second Example Embodiment

Figure 4:
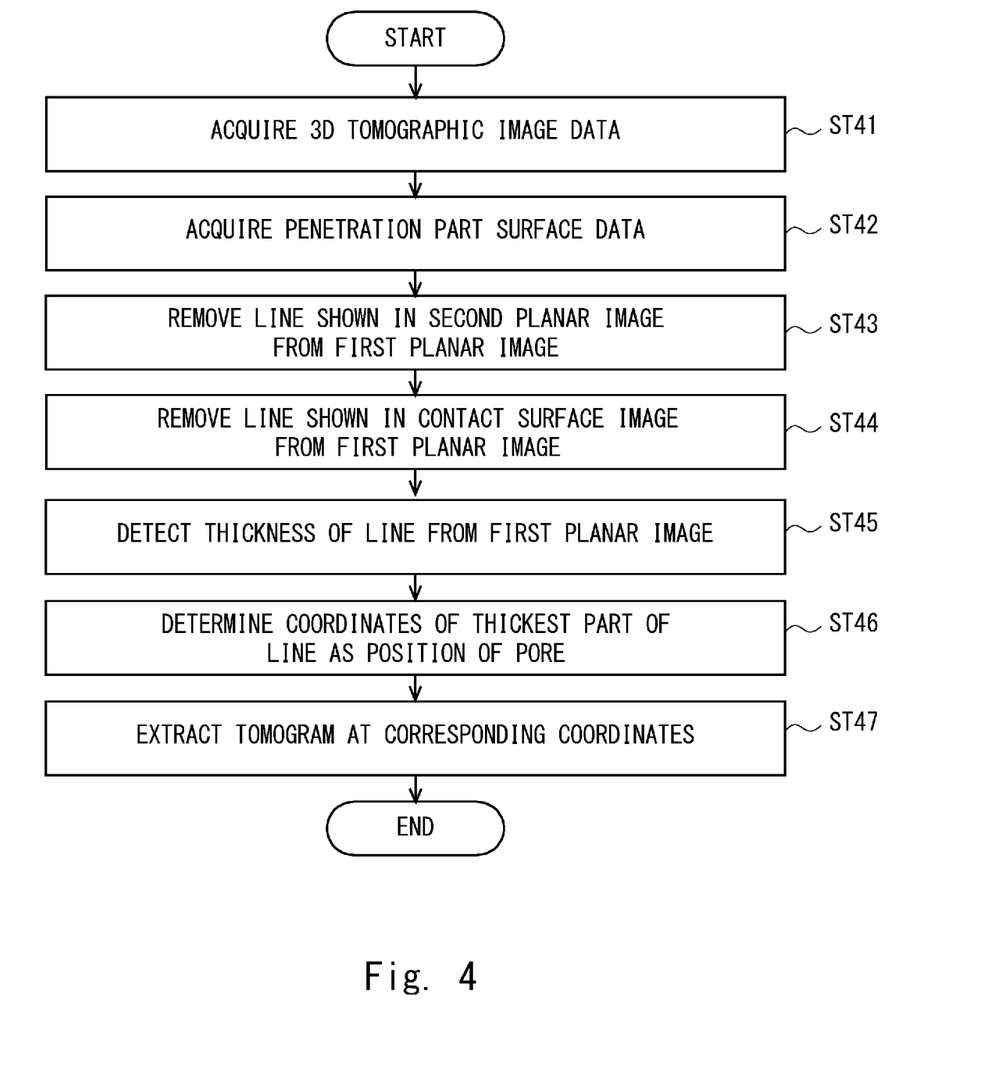
FIG. 4 is a flowchart showing an optical measurement method according to a second example embodiment.

An optical measurement method according to a second example embodiment will be described with reference to FIGS. 4 to 13. FIG. 4 is a flowchart showing the optical measurement method according to the second example embodiment. It should be noted that the drawings shown in FIGS. 5 to 13 are merely examples, so that the optical measurement method according to the second example embodiment should not be limited to them.

Figure 5:
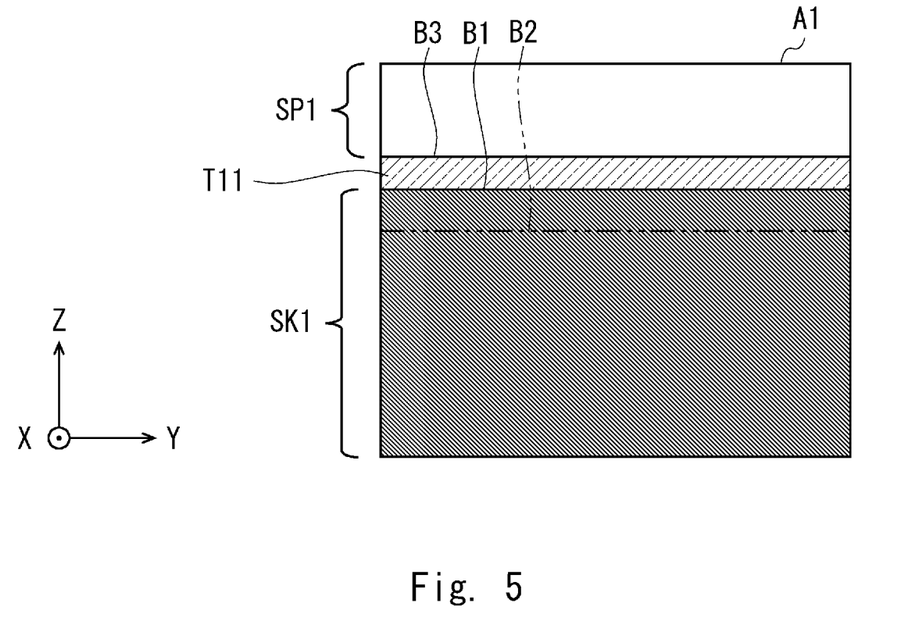
FIG. 5 is a schematic diagram showing an example of a tomogram.
Figure 6:
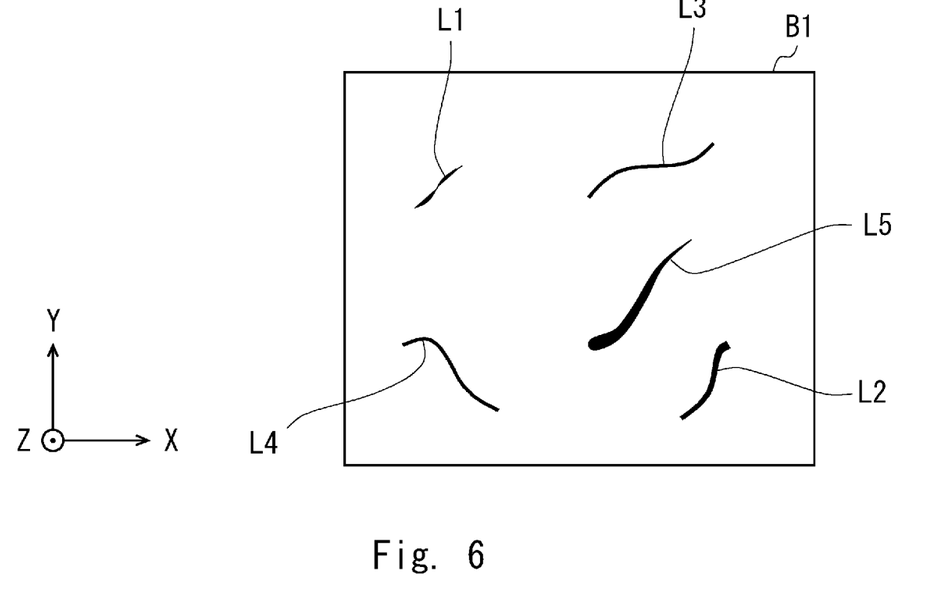
FIG. 6 is a schematic diagram showing an example of the outermost surface of a skin.
Figure 7:
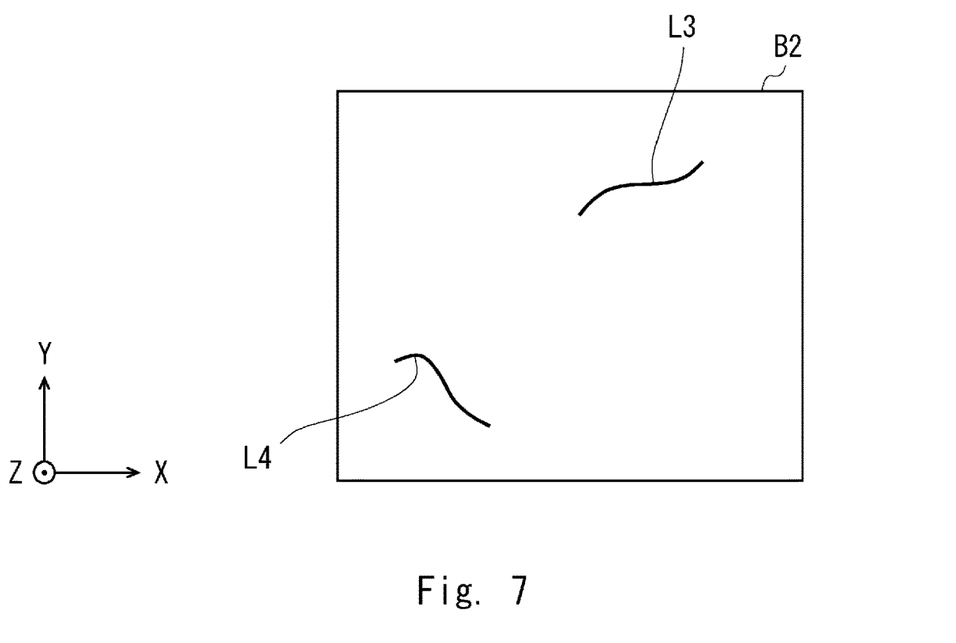
FIG. 7 is a schematic diagram showing an example of a planar diagram at a predetermined depth from the outermost surface of a skin.
Figure 8:
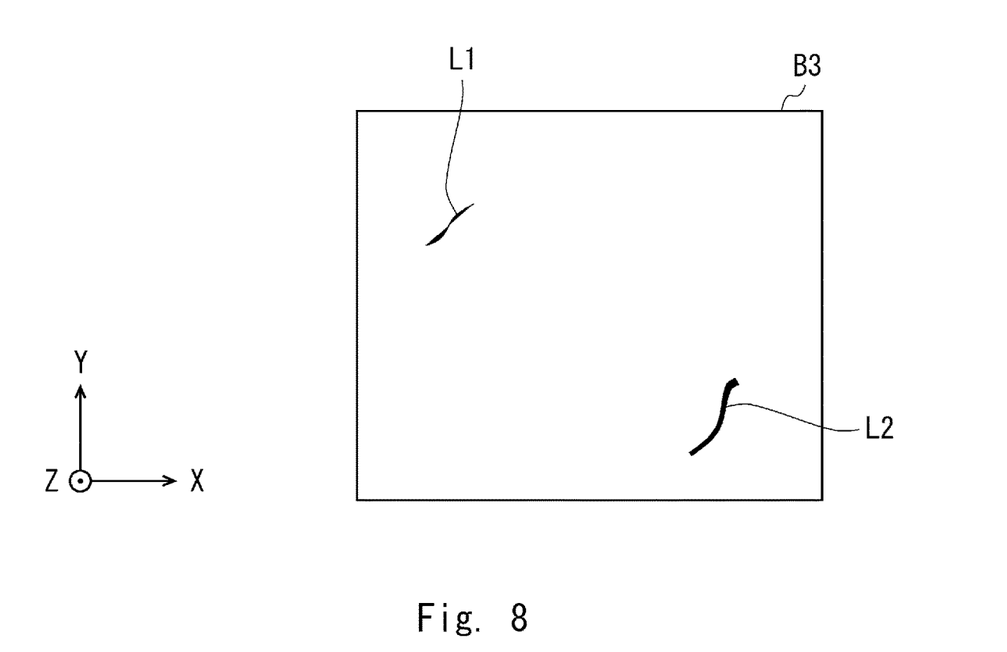
FIG. 8 is a schematic diagram showing an example of a surface of a penetration part on the side on which a measuring instrument is located.
Figure 9:
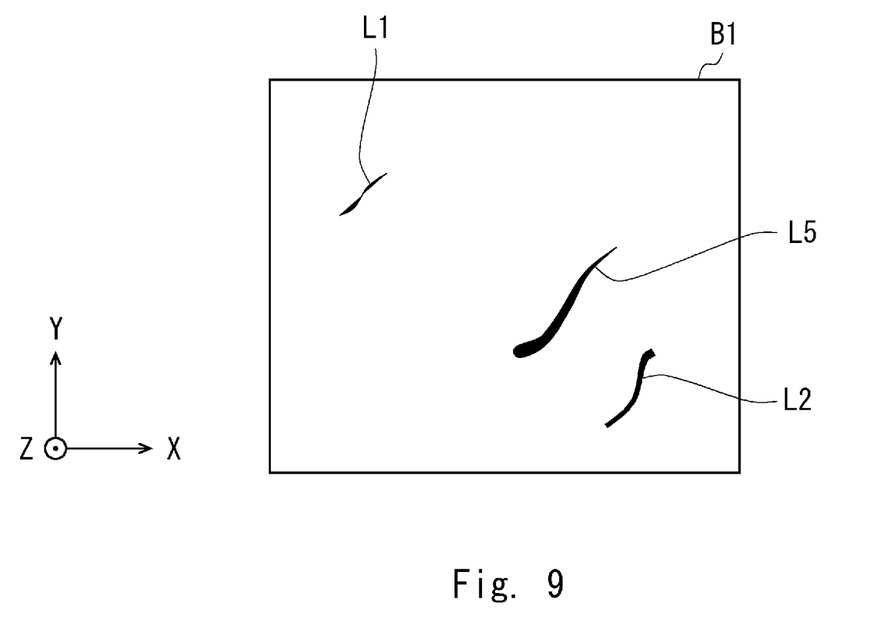
FIG. 9 is a schematic diagram showing an example of a planar diagram from which lines corresponding to wrinkles have been removed.
Figure 10:
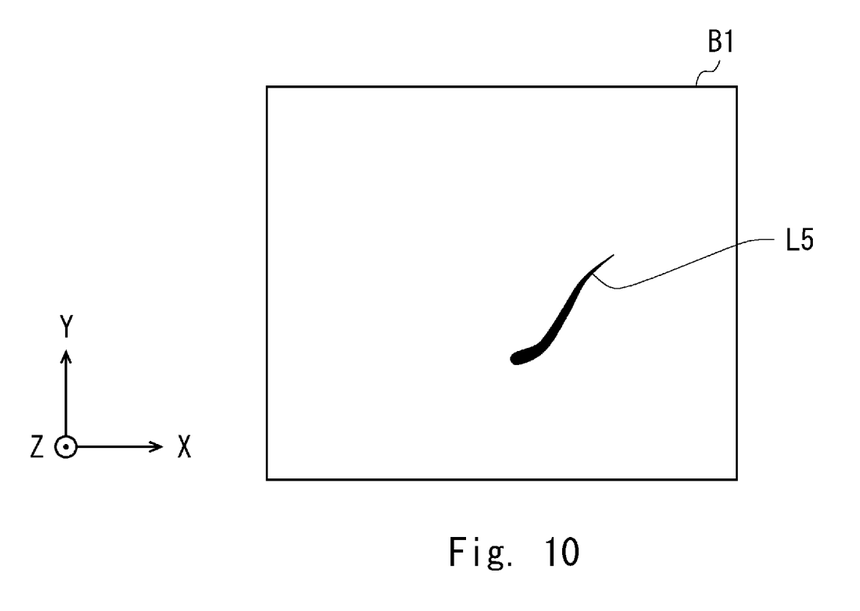
FIG. 10 is a schematic diagram showing an example of a planar diagram from which lines corresponding to foreign objects have been removed.
Figure 11:
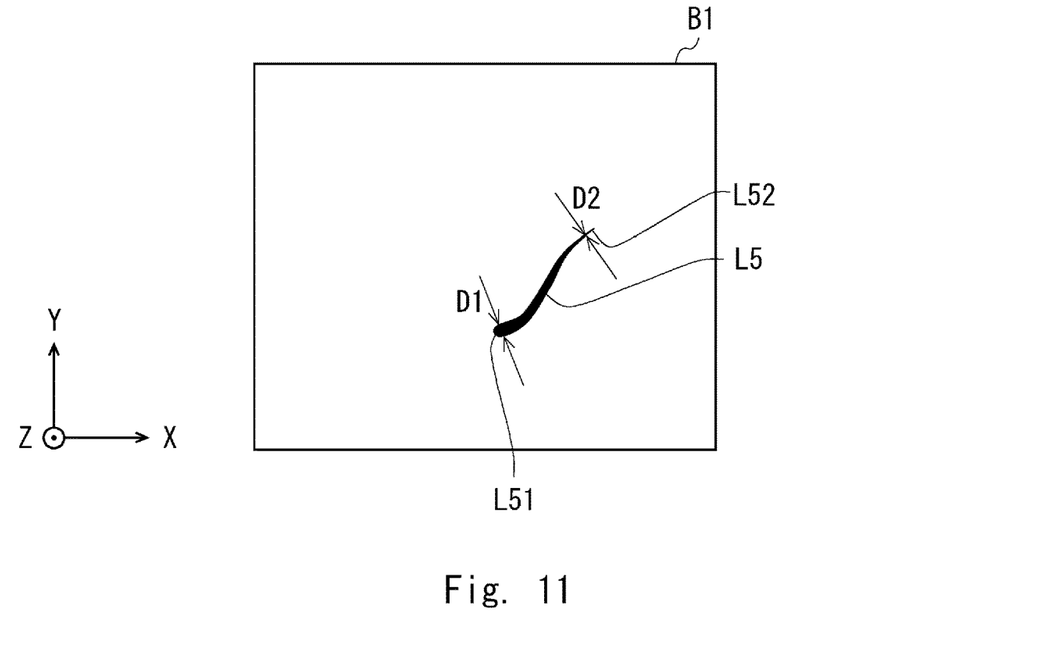
FIG. 11 is a schematic diagram showing a method for measuring the thickness of a remaining line.
Figure 12:
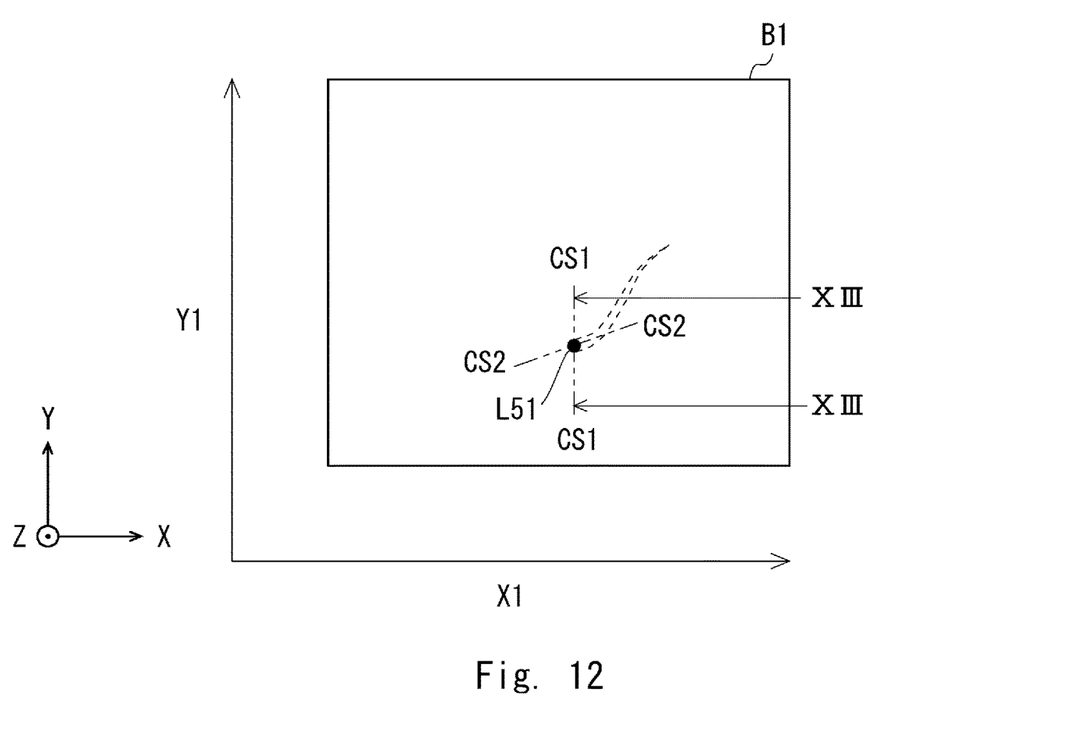
FIG. 12 is a schematic diagram showing a method for measuring coordinates of the position of a specified pore.
Figure 13:
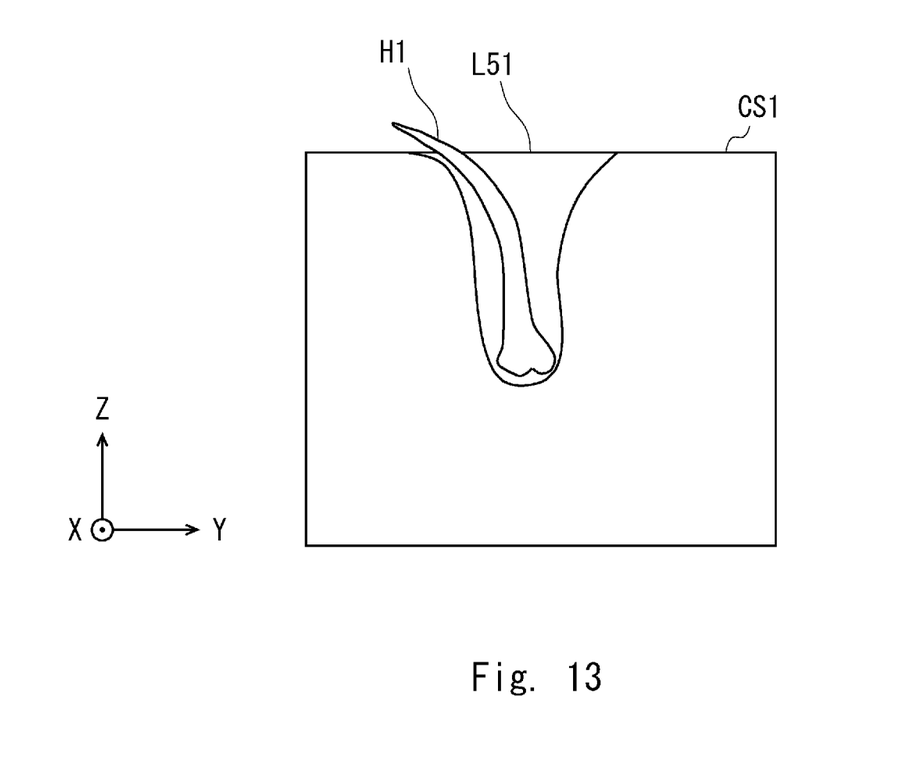
FIG. 13 is a schematic diagram showing an example of a tomogram including the specified pore.

FIG. 5 is a schematic diagram showing an example of a tomogram. FIG. 6 is a schematic diagram showing an example of the outermost surface of a skin. FIG. 7 is a schematic diagram showing an example of a planar diagram at a predetermined depth from the outermost surface of the skin. FIG. 8 is a schematic diagram showing an example of a surface of a penetration part on the side on which a measuring instrument is located. FIG. 9 is a schematic diagram showing an example of a planar diagram from which lines corresponding to wrinkles have been removed. FIG. 10 is a schematic diagram showing an example of a planar diagram from which lines corresponding to foreign objects have been removed. FIG. 11 is a schematic diagram showing a method for measuring the thickness of a remaining line. FIG. 12 is a schematic diagram showing a method for measuring coordinates of the position of a specified pore. FIG. 13 is a schematic diagram showing an example of a tomogram including the specified pore. Further, in FIG. 13, hatching is omitted to clarifying the drawing.

Note that, needless to say, right-handed xyz-coordinate systems shown in FIG. 5 and in other drawings are shown just for the sake of convenience to show the positional relationship among objects (e.g., tissues, foreign objects, and the like). In general, the z-axis positive direction is the vertically upward direction, and the xy-plane is parallel to the horizontal plane. These definitions apply to other drawings.

First 3D tomographic image data is acquired from a skin by using optical coherence tomography (Step ST41). The first 3D tomographic image data is composed of a plurality of image data in a plurality of planes at respective predetermined depths. Such image data includes, for example, image data in a first plane B1 at a first depth and image data in a second plane B2 at a second depth. Further, it is possible to generate a tomogram based on such a plurality of image data.

A tomogram A1, which is an example of the above-described tomogram, will be described with reference to FIG. 5. As shown in FIG. 5, a skin SK1, a penetration part T11, and a space SP1 are shown in the tomogram A1. The penetration part T11 is in contact with the skin SK1, and the space SP1 extends over the penetration part T11. A measuring instrument (not shown) is disposed above the space SP1 (in this example, on the positive side in the Z-axis direction of the space SP1).

As shown in FIG. 6, lines L1 to L5 can be observed in the first plane B1. Note that the lines L1 and L2 are foreign objects. The lines L3 and L4 are wrinkles. The line L5 is a hair. The wrinkles and the hairs originate in the skin, on which the measurement is performed according to the optical measurement method. However, it is difficult to determine which of a foreign object, a wrinkle, and a hair each of the lines L1 to L5 is based solely on the image in the first plane B1.

As shown in FIG. 7, the lines L3 and L4 can also be observed in the second plane B2. In contrast, the lines L1, L2 and L5 could not be observed in the second plane B2.

Next, penetration part surface image data is acquired from the penetration part T11 by using optical coherence tomography (Step ST42). In the optical coherence tomography, the measuring instrument, which is a measuring instrument of (i.e., a part of) an optical interferometer, is positioned so as to be opposed to the skin with the penetration part interposed therebetween. The penetration part surface image data is image data in a penetration part surface B3 of the penetration part T11 on the side on which the measuring instrument is disposed (see FIG. 5). For example, as shown in FIG. 8, the lines L1 and L2 can be observed in the penetration part surface B3. In contrast, the lines L3, L4 and L5 could not be observed in the second plane B2.

Next, the lines shown in the second plane B2 (see FIG. 7) are removed from the image in the first plane B1 (see FIG. 6) (Step ST43). For example, the lines L3 and L4 shown in the first plane B1 are removed. As shown in FIG. 9, the lines L1, L2 and L5 can be observed in the first plane B1.

Next, the lines shown in the penetration part surface B3 (see FIG. 8) are removed from the image in the first plane B1, from which the lines have been removed as described above, (see FIG. 9) (Step ST44). For example, the lines L1 and L2 are removed from the first plane B1. As shown in FIG. 10, the line L5 can be observed in the first plane B1.

Next, the thickness of the line shown in the image in the first plane B1 is detected (Step ST45). For example, as shown in FIG. 11, a thickness D1 at one end L51 of the line L5 and a thickness D2 at the other end L52 of the line L5 are measured.

Next, similarly to the steps ST23 and ST34, coordinates of the thickest part of the line, of which the thicknesses have been detected as described above, are determined as the position of the pore (Step ST46). For example, as shown in FIG. 11, the thickness D1 at the one end L51 of the line L5 is larger than the thickness D2 at the other end L52 thereof. Therefore, the one end L51 is determined as the position of the pore.

Lastly, a tomogram at the coordinates, which have been determined as the position of the pore, is extracted (Step ST47). The tomogram shows a cross section of the hair, the pore, and areas around them. For example, as shown in FIG. 12, a tomogram CS1 at the one end L51, which has been determined as the position of the pore, is extracted. As shown in FIG. 13, the hair H1 can be observed in the tomogram CS1. The plane of the tomogram CS1 is parallel to the YZ-plane. The one end L51 corresponds to the position of the pore of the hair H1. The hair H1 and the periphery of the hair H1 is preferably displayed in a 3D (three-dimensional) manner as desired, so that the user or the like can recognize (e.g., check) the pore of the hair H1 in a more detailed manner.

Thorough the above-described processes, it is possible to specify the position of the pore, and also possible to acquire a tomogram showing the hair and the like. By checking the tomogram, a user confirms that the determined coordinates correspond to the position of the pore. That is, it is possible accurately specify the position of the pore.

Note that, a plurality of tomogram data showing the pore may be acquired based on the inclination of the hair at the pore in the step ST47. For example, as shown in FIG. 12, a tomogram CS2 at the one end L51 may be extracted. The extraction of the tomogram CS2 is preferred because the plane of the tomogram CS2 is parallel to the direction of the line L5 on the plane (in this case, on the XY-plane), so that the tomogram CS2 may show the whole line L5 in a comprehensive manner.

Further, the position of the pore may be specified in second 3D tomographic image data different from the first 3D tomographic image data acquired in the step ST41 by using the above-described optical measurement method. The part of the skin shown in the second 3D tomographic image data is different from the part of the skin shown in the first 3D tomographic image data. Further, the part of the skin shown in the second 3D tomographic image data includes the position of the pore specified from the first 3D tomographic image data. Further, the position of the pore, such as the pore corresponding to the line L5, specified by the first 3D tomographic image data may be compared with the position thereof specified by the second 3D tomographic image data. In this way, it is possible to improve the accuracy of the detection of the position of the pore.

(Control Configuration)

Figure 14:
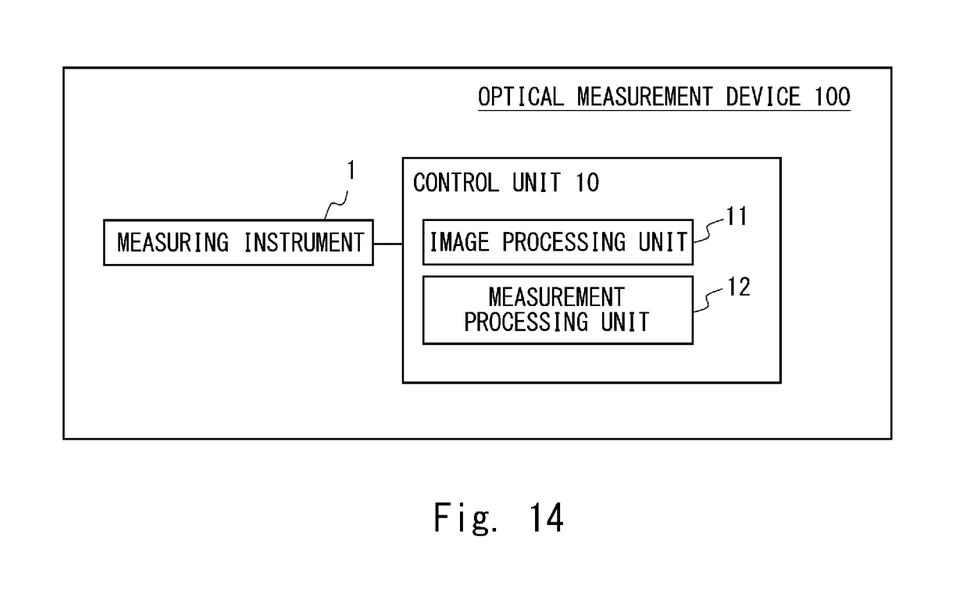
FIG. 14 is a control block diagram of an optical measurement apparatus.

An optical measurement apparatus 100 shown in FIG. 14 can be used in the above-described optical measurement method according to the third example embodiment. FIG. 14 is a control block diagram of the optical measurement apparatus.

As shown in FIG. 14, the optical measurement apparatus 100 includes a measuring instrument 1 and a control unit 10.

The measuring instrument 1 is a measuring instrument of (i.e., a part of) an optical interferometer. The measuring instrument 1 measures interference light that is generated by combining two light beams with each other and thereby making them interfere with each other. Specifically, one light beam is divided into two light beams traveling along two paths. One of the divided light beams is reflected on an object to be measured, and the other divided light beam is reflected by a reference mirror. Then, these two light beams are combined with each other. The object to be measured is, for example, a skin or the like. The measuring instrument 1 generates first 3D tomographic image data of the skin by, for example, performing brightness conversion on signals that are obtained based on the above-described measured interference light.

The control unit 10 includes an image processing unit 11 and a measurement processing unit 12.

The image processing unit 11 acquires the first 3D tomographic image data of the skin from the measuring instrument 1. The image processing unit 11 generates image data by performing image processing on planar images included in the first 3D tomographic image data. This image processing is, for example, a process in which images included in the first 3D tomographic image data are compared with each other, and lines shown in one of the images are deleted from the other image. Alternatively, this image processing may be, for example, a process in which a tomographic image is generated based on a plurality of planar images.

The measurement processing unit 12 acquires the first 3D tomographic image data from the measuring instrument 1. Further, the measurement processing unit 12 acquires the image data for which the image processing unit 11 has performed the image processing. Further, the measurement processing unit 12 detects the thickness of a line from the acquired first 3D tomographic image data or the acquired image data. The measurement processing unit 12 may, for example, detect the thicknesses of a plurality of parts of the line. The measurement processing unit 12 may detect the thickest part among the plurality of parts of the line of which the thicknesses have been detected.

The control unit 10 may include, as a hardware configuration, for example, an arithmetic circuit including a CPU (Central Processing Unit), and a storage device or the like including a program memory, a data memory, and other memories such as a RAM (Random Access Memory) and a ROM (Read Only Memory). The control unit 10 acquires data from each component of the optical measurement apparatus 100 such as the measuring instrument 1, and calculates various data by the arithmetic circuit according to a program stored in the storage device. The control unit 10 may function as the image processing unit 11 and the measurement processing unit 12 according to the result of the calculation.

Note that the optical measurement apparatus 100 may include a display unit as required. The display unit displays a tomographic image and a planar image as appropriate based on the above-described first 3D tomographic image data. Further, the display unit displays an image-processed tomographic image, an image-processed planar image, and the like based on the above-described image-processed image data.

(Relationship Between Depth of Planar Image and Structure of Skin)

Figure 15:
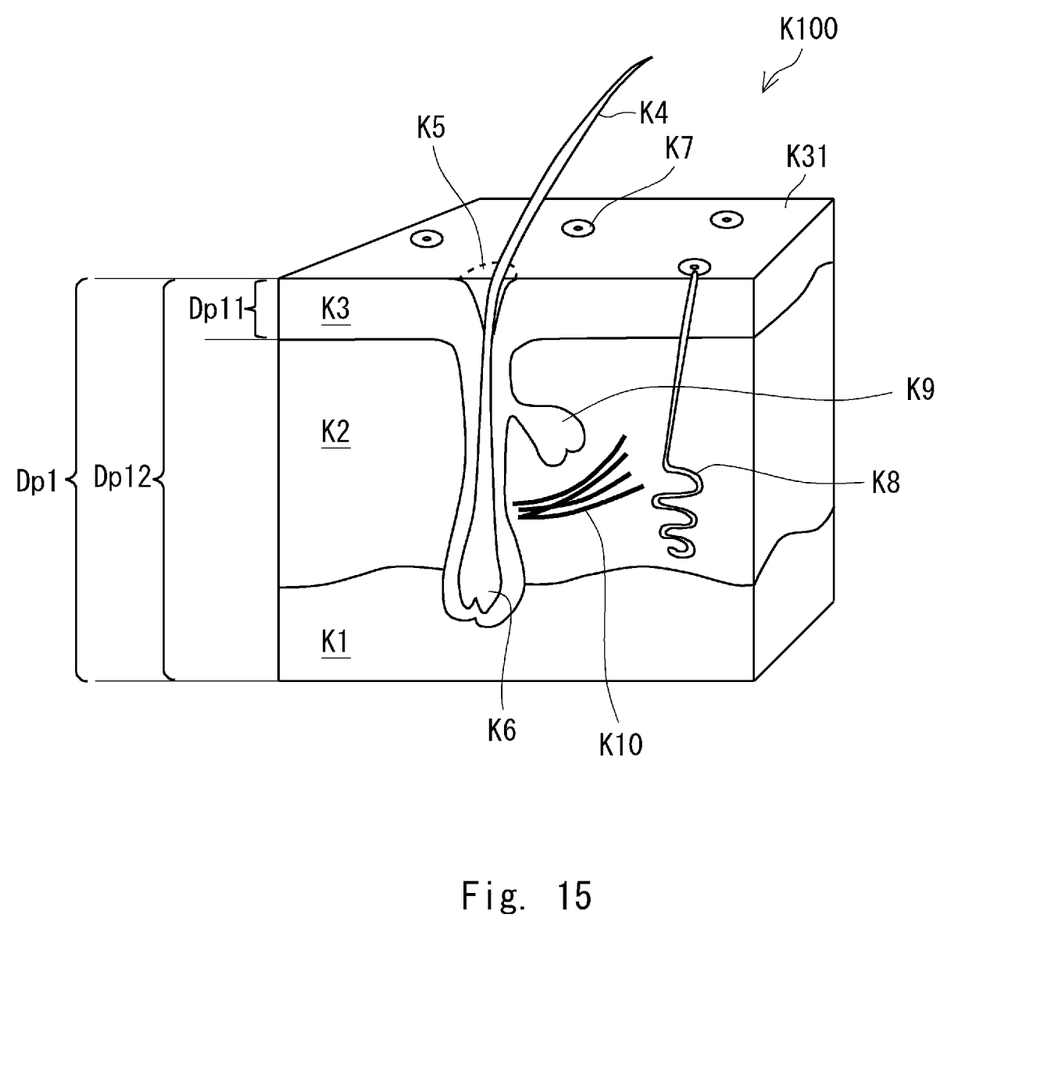
FIG. 15 is a schematic diagram showing an example of the outermost surface of a skin and a cross section thereof.

Next, the relationship between the depths of the first and second planar images and the structure of the skin in the step ST11 (see FIG. 1) of the optical measurement method according to the example embodiment will be described with reference to FIG. 15. FIG. 15 is a schematic diagram showing an example of the outermost surface of a skin and a cross section thereof. Further, in FIG. 15, hatching is omitted to clarifying the drawing.

In most cases, a skin has a structure similar to that of the skin K100 shown in FIG. 15. As shown in FIG. 15, the skin K100 includes a subcutaneous tissue K1, a dermis K2, and an epidermis K3, and they have a layered structure in which they are layered in this order. The thickness of the dermis K2 is, for example, smaller than 2 mm. The thickness of the epidermis K3 is, for example, 0.2 mm. The epidermis K3 includes the outermost surface K31. The outermost surface K31 is in direct contact with the external environment. Pores K5 and sweat pores K7 are located (i.e., are present) in the outermost surface K31. A hair K4 extends (grows) from the pore K5. A hair follicle K6 of the hair K4 is located at the bottom of the pore K5, and the bottom of the pore K5 is located inside the subcutaneous tissue K1 or inside the dermis K2. An eccrine sweat gland K8 is located inside the dermis K2 and is connected to the sweat pore K7. A sebaceous gland K9 and an arrector muscle K10 are located inside the dermis K2.

In a step ST11, first 3D tomographic image data that is acquired from the skin K100 by using optical coherence tomography is used. This first 3D tomographic image data includes a plurality of planar images including a planar image in the outermost surface of the skin and those inside the skin.

Depths Dp1 of the plurality of planar images may be in a range from the outermost surface K31 to the subcutaneous tissue K1, and are, for example, in a range from the outermost surface K31 to a depth of 5 mm.

The depth Dp11 of the first planar image is, for example, in a range from the outermost surface K31 to the depth of the inside of the epidermis K3. The depth Dp1l of the first planar image is, for example, in a range from the outermost surface K31 to 30 μm (=0.030 mm).

The depth Dp12 of the second planar image may be in a range from the outermost surface K31 to the inside of the subcutaneous tissue K1, and is, for example, in a range from the outermost surface K31 to a depth of 5 mm.

The depth Dp12 of the second planar image is preferably to the inside of the epidermis K3. The epidermis K3 is likely to include no hair follicle K6, no eccrine sweat gland K8, no sebaceous gland K9, and no arrector muscle K10. Therefore, the depth Dp12 is preferably located inside the epidermis K3, so that the second planar image is not affected by the hair follicle K6, the eccrine sweat gland K8, the sebaceous gland K9, and the arrector muscle K10. Therefore, it is preferable because the second planar image can reliably show wrinkles, thus making it possible to accurately detect the position of a pore.

The depth Dp12 of the second planar image is preferably to the inside of the inside of the dermis K2. The dermis K2 is likely to include no pore K5 and no sweat pore K7. Therefore, the depth Dp12 is preferably to the inside of the dermis K2, so that the second planar image is not affected by the pore K5 and the sweat pore K7. Therefore, it is preferable because the second planar image can reliably show wrinkles, thus making it possible to accurately detect the position of a pore.

The depth Dp12 of the second planar image is preferably to the inside of the subcutaneous tissue K1. When the depth Dp12 is to the inside of the subcutaneous tissue K1, it is likely that no pore K5, no sweat pore K7, no eccrine sweat gland K8, no sebaceous gland K9, and no arrector muscle K10 are present in the subcutaneous tissue K1. Therefore, the depth Dp12 is preferably to the inside of the subcutaneous tissue K1, so that the second planar image is not affected by the pore K5, the sweat pore K7, the eccrine sweat gland K8, the sebaceous gland K9, and the arrector muscle K10. Therefore, it is preferable because the second planar image can reliably show wrinkles, thus making it possible to accurately detect the position of a pore.

Other Example Embodiment

In the above example embodiment, the present invention has been described as an optical measurement method, but the present invention is not limited the optical measurement method. The optical measurement apparatus 100 (see FIG. 14) can preferably perform the optical measurement method. In the present invention, an arbitrary method or an arbitrary step(s) can also be implemented by having a CPU (Central Processing Unit) execute a computer program.

Figure 16:
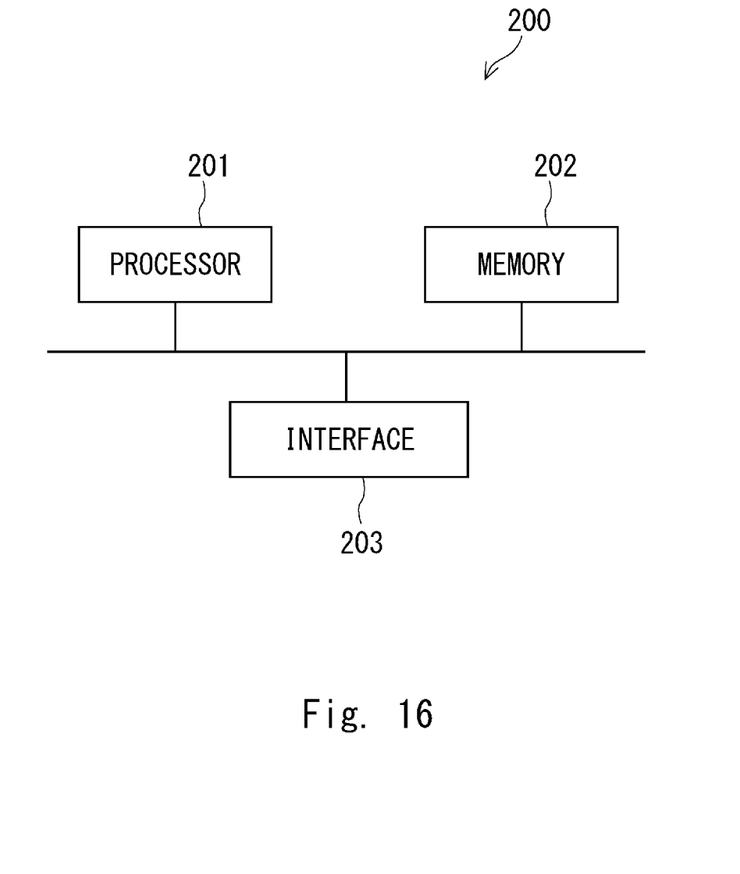
FIG. 16 shows an example of a hardware configuration included in an optical measurement apparatus.

The optical measurement apparatus 100 may have the below-described hardware configuration. FIG. 16 shows an example of a hardware configuration included in the optical measurement apparatus 100.

An apparatus 200 shown in FIG. 16 includes an interface 203, a processor 201, and a memory 202. The control unit 10, the image processing unit 11, and the measurement processing unit 12 (see FIG. 14) described in the above-described example embodiment are implemented by having the processor 201 load a control program stored in the memory 202 and execute the loaded control program. That is, the aforementioned control program is a program for causing the processor 201 to function as the control unit 10 shown in FIG. 14 or a part thereof. It can be said that the aforementioned control program is a program for performing processes performed in the control unit 10 shown in FIG. 14 or some of the processes.

The above-described program can be stored and provided to a computer using any type of non-transitory computer readable media. Non-transitory computer readable media includes any type of tangible storage media. Examples of non-transitory computer readable media include magnetic storage media (floppy disks, magnetic tapes, hard disk drives), optical magnetic storage media (e.g., magneto-optical disks), CD-ROM (Read Only Memory), CD-R, CD-R/W, and semiconductor memories (e.g., mask ROM, PROM (Programmable ROM), EPROM (Erasable PROM), flash ROM, and RAM (Random Access Memory)). Further, the program may be provided to a computer using any type of transitory computer readable media. Examples of transitory computer readable media include electric signals, optical signals, and electromagnetic waves. Transitory computer readable media can provide the program to a computer via a wired communication line (e.g., electric wires, and optical fibers) or a wireless communication line.

Although the present invention has been described with reference to example embodiments (and examples), the present invention is not limited to the above-described example embodiments (and examples). The configuration and details of the present invention may be modified within the scope of the present invention in various ways that can be understood by those skilled in the art. For example, in the above-described example embodiments, 3D tomographic image data is acquired from a skin by using optical coherence tomography. However, 3D tomographic image data or data having a structure similar thereto may be acquired from a skin by using an optical measurement method such as an optical ultrasonic technology or a technology using a confocal microscope.

Further, the optical measurement method according to the above-described example embodiment, and the above-described first and second example embodiments can be used in a wide variety of industries. Examples of such industries include beauty care and medical care.

REFERENCE SIGNS LIST

100 OPTICAL MEASUREMENT DEVICE
1 MEASURING INSTRUMENT
10 CONTROL UNIT
11 IMAGE PROCESSING UNIT
12 MEASUREMENT PROCESSING UNIT
200 APPARATUS
201 PROCESSOR
202 MEMORY
203 INTERFACE
A1, A11 TOMOGRAM
B1, B2, B11, B12 PLANE
B11a, B12a, B13a AREA
B3, B13 PENETRATION PART SURFACE
CS1, CS2 TOMOGRAM
H1 HAIR
K100 SKIN
K1 SUBCUTANEOUS TISSUE
K2 DERMIS
K3 EPIDERMIS
K31 OUTERMOST SURFACE
K4 HAIR
K5 PORE
K6 HAIR FOLLICLE
L1-L5, L11-L14 LINE
L51 ONE END
L52 OTHER END
SK1, SK11 SKIN
SP1, SP11 SPACE
ST1-ST, ST11-ST13, ST21-ST23, ST31-ST34, ST41-ST47 STEP
T11, T21 PENETRATION PART

What is claimed is:

1. An optical measurement method comprising:
   a step of removing, from a first planar image at a first depth in a first three-dimensional tomographic image data acquired from a skin by using optical coherence tomography, a line shown in a second planar image at a second depth deeper than the first depth; and
   a step of specifying a position of a pore from the first planar image from which the line has been removed.

2. The optical measurement method according to claim 1, wherein in the step of specifying the position of the pore, the position of the pore is specified by detecting a thickness of a line shown in the first planar image.

3. The optical measurement method according to claim 1, further comprising:
   a step of positioning a measuring instrument of an optical interferometer so as to be opposed to the skin with a penetration part interposed therebetween, and acquiring a penetration part surface image showing a surface of the penetration part by using the optical coherence tomography; and a step of removing a line shown in the penetration part surface image from the first planar image.

4. The optical measurement method according to claim 1, further comprising, after performing the step of specifying the position of the pore, a step of displaying a hair of which the position of the pore has been specified in a three-dimensional manner.

5. The optical measurement method according to claim 1, further comprising:

a step of acquiring at least one second 3D tomographic image data showing a part of the skin different from a part of the skin shown by the first 3D tomographic image data, the part of the skin shown by the second 3D tomographic image data including the position of the pore specified from the first 3D tomographic image data;

a step of specifying the position of the pore from the second 3D tomographic image data; and a step of comparing the position of the pore specified from the first 3D tomographic image data with the position of the pore specified from the second 3D tomographic image data.

6. The optical measurement method according to claim 1, further comprising a step of acquiring a plurality of tomogram data each showing the pore based on an inclination of the hair at the pore.

7. The optical measurement method according to claim 1, wherein the first planar image shows a surface of an epidermis of the skin.

8. The optical measurement method according to claim 1, wherein the second planar image shows a plane located inside an epidermis of the skin.

9. The optical measurement method according to claim 1, wherein the second planar image shows a plane located inside a dermis of the skin.

10. The optical measurement method according to claim 1, wherein the second planar image shows a plane located inside a subcutaneous tissue of the skin.

11. An optical measurement apparatus comprising:

an image processing unit configured to remove, from a first planar image at a first depth in a first three-dimensional tomographic image data acquired from a skin by using optical coherence tomography, a line shown in a second planar image at a second depth deeper than the first depth; and a measurement processing unit configured to specify a position of a pore from the first planar image from which the line has been removed.

12. A non-transitory computer readable medium storing a program for causing a computer functioning as an optical measurement apparatus to perform:

a step of removing, from a first planar image at a first depth in a first three-dimensional tomographic image data acquired from a skin by using optical coherence tomography, a line shown in a second planar image at a second depth deeper than the first depth; and a step of specifying a position of a pore from the first planar image from which the line has been removed.

* * * * *